US011344211B2

(12) United States Patent
Li et al.

(10) Patent No.: US 11,344,211 B2
(45) Date of Patent: May 31, 2022

(54) HMM-BASED ADAPTIVE SPECTROGRAM TRACK METHOD

(71) Applicant: Intel Corporation, Santa Clara, CA (US)

(72) Inventors: Tingqian Li, Songjiang District (CN); Zhaohui Meng, Minhang District (CN); Jinkui Ren, Shanghai (CN)

(73) Assignee: Intel Corporation, Santa Clara, CA (US)

( * ) Notice: Subject to any disclaimer, the term of this patent is extended or adjusted under 35 U.S.C. 154(b) by 843 days.

(21) Appl. No.: 16/061,616

(22) PCT Filed: Dec. 23, 2015

(86) PCT No.: PCT/CN2015/098377
§ 371 (c)(1),
(2) Date: Jun. 12, 2018

(87) PCT Pub. No.: WO2017/107085
PCT Pub. Date: Jun. 29, 2017

(65) Prior Publication Data
US 2020/0305735 A1     Oct. 1, 2020

(51) Int. Cl.
*A61B 5/02*     (2006.01)
*A61B 5/024*     (2006.01)
(Continued)

(52) U.S. Cl.
CPC ........ *A61B 5/02416* (2013.01); *A61B 5/0075* (2013.01); *A61B 5/6802* (2013.01); *A61B 5/7221* (2013.01); *G06K 9/6297* (2013.01)

(58) Field of Classification Search
USPC ................................................ 600/508–509
See application file for complete search history.

(56) References Cited

U.S. PATENT DOCUMENTS 6,980,913 B2    12/2005    Meir
7,225,013 B2    5/2007    Geva et al.
(Continued)

FOREIGN PATENT DOCUMENTS

CN     101111195 A     1/2008
CN     102715897 A     10/2012
(Continued)

OTHER PUBLICATIONS

"Chinese Application Serial No. 201530085432.X, Response filed Jan. 26, 2021 to Office Action dated Sep. 11, 2020", w/ Current English Claims, 10 pgs.
(Continued)

*Primary Examiner* — Nicole F Lavert
(74) *Attorney, Agent, or Firm* — Schwegman Lundberg & Woessner, P.A.

(57) ABSTRACT

Embodiments of a system and method for heart rate monitoring are generally described herein. A method may include receiving, at a device, a spectrogram including a plurality of bins of represented frequencies corresponding to potential heart rate measurements, selecting a bin of frequencies from the plurality of bins of represented frequencies with an average power that exceeds average powers of remaining bins of frequencies of the plurality of bins of represented frequencies, determining whether a frequency of the bin of frequencies represents a valid heart rate based on the average power and a past valid heart rate, and in response to determining that the frequency represents a valid heart rate, outputting a heart rate corresponding to the frequency.

24 Claims, 5 Drawing Sheets

(51) Int. Cl.
*A61B 5/00* (2006.01)
*G06K 9/62* (2022.01)

(56) References Cited

U.S. PATENT DOCUMENTS

| | | | | |
|---|---|---|---|---|
| 2002/0193670 A1* | 12/2002 | Garfield | ............... | A61B 5/4362 |
| | | | | 600/304 |
| 2008/0009917 A1* | 1/2008 | Rossing | ............... | A61B 5/4052 |
| | | | | 607/44 |
| 2008/0108906 A1* | 5/2008 | Chang | ................... | A61B 5/7257 |
| | | | | 600/515 |
| 2009/0275847 A1 | 11/2009 | Karasudari | | |
| 2010/0113893 A1* | 5/2010 | Cohen | ..................... | A61B 5/349 |
| | | | | 600/301 |
| 2010/0261977 A1* | 10/2010 | Seely | ..................... | G16H 15/00 |
| | | | | 600/300 |
| 2011/0275910 A1 | 11/2011 | Amos et al. | | |
| 2014/0073486 A1* | 3/2014 | Ahmed | .............. | A61B 5/02427 |
| | | | | 482/9 |
| 2015/0150515 A1* | 6/2015 | Strachan | ................ | A61B 5/0205 |
| | | | | 600/301 |
| 2015/0272509 A1 | 10/2015 | Kwon | | |
| 2016/0022220 A1* | 1/2016 | Lee | .................... | A61B 5/02433 |
| | | | | 600/479 |

FOREIGN PATENT DOCUMENTS

| | | |
|---|---|---|
| CN | 103230267 A | 8/2013 |
| CN | 103431851 | 12/2013 |
| CN | 105105737 A | 12/2015 |
| CN | 108430320 B | 6/2021 |
| WO | 2012086175 | 6/2012 |
| WO | WO-2017107085 A1 | 6/2017 |

OTHER PUBLICATIONS

"International Application Serial No. PCT/CN2015/098377, International Search Report dated Oct. 8, 2016", 4 pgs.

"International Application Serial No. PCT/CN2015/098377, Written Opinion dated Oct. 8, 2016", 4 pgs.

Nilsson, Frida, et al., "Frequency Tracking of Atrial Fibrillation using Hidden Markov Models", Proceedings of the 28th IEEE EMBS Annual International Conference, (Sep. 3, 2006), 1406-1409.

"Chinese Application Serial No. 201580085432.X, Office Action dated Sep. 11, 2020", w English translation, 19 pgs.

* cited by examiner

HMM-BASED ADAPTIVE SPECTROGRAM TRACK METHOD

CLAIM OF PRIORITY

This patent application is a U.S. National Stage Application under 35 U.S.C. 371 from International Application No. PCT/CN2015/098377, filed Dec. 23, 2015, published as WO 2017/107085, which is incorporated herein by reference.

BACKGROUND

According to some technical analysts, there will be over 50 billion connected "things" by the year 2020. This will completely transform current infrastructures and will drive new innovations in industry, products, and services. Internet-of-Things (IoT) is term that represents devices and systems that communicate over a network, such as the internet. The devices and systems may include sensors. IoT devices may include a heart rate sensor to receive an optical signal. The optical sensors are often negatively influenced by interference. Current methods of determining heart rate from the optical sensors produce unreliable results.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Heart rate monitoring is used for monitoring health, exercise progress, general fitness, and fun. An example of heart rate monitoring includes heart rate tracking. Heart rate tracking is the final step of a photoplethysmography (PPG) based heart rate monitoring technique. The PPG-based heart rate monitoring technique uses a sensor, such as a pulse oximeter to measure changes in light absorption. The sensor outputs an optical signal that is converted to a spectrogram. From the spectrogram, an output may include a final heart rate estimate. In an example, white noise may interfere with the optical signal. In addition to the white noise generated by the optical sensing process, motion artifact (MA) interference may also corrupt the spectrogram. In an example, adaptive filters done in preprocessing steps may reduce these noises, but complete removal may not be possible. The remaining noise level may still make the PPG-based heart rate monitoring technique fail. For example, searching frequency components with maximum power may cause dramatic and unreal jumping in the resulting heart rate output, and the accuracy may be unacceptably low.

A technique includes searching and tracking to locate a possible heart rate by searching for an evident frequency component that is varying reasonably slowly and continuously for some predefined period of time. The technique may iteratively track from a previous estimate to the next one. The tracking process utilizes the fact that a true heart rate is varying continuously with limited changing rate, so when new spectra is sampled, heart rates near the previous estimate may be used rather than searching through the whole spectrum.

This technique run on only a single path risks losing other possible heart rates. An improved technique may track multiple paths concurrently and output one with a maximum likelihood.

Figure 1:
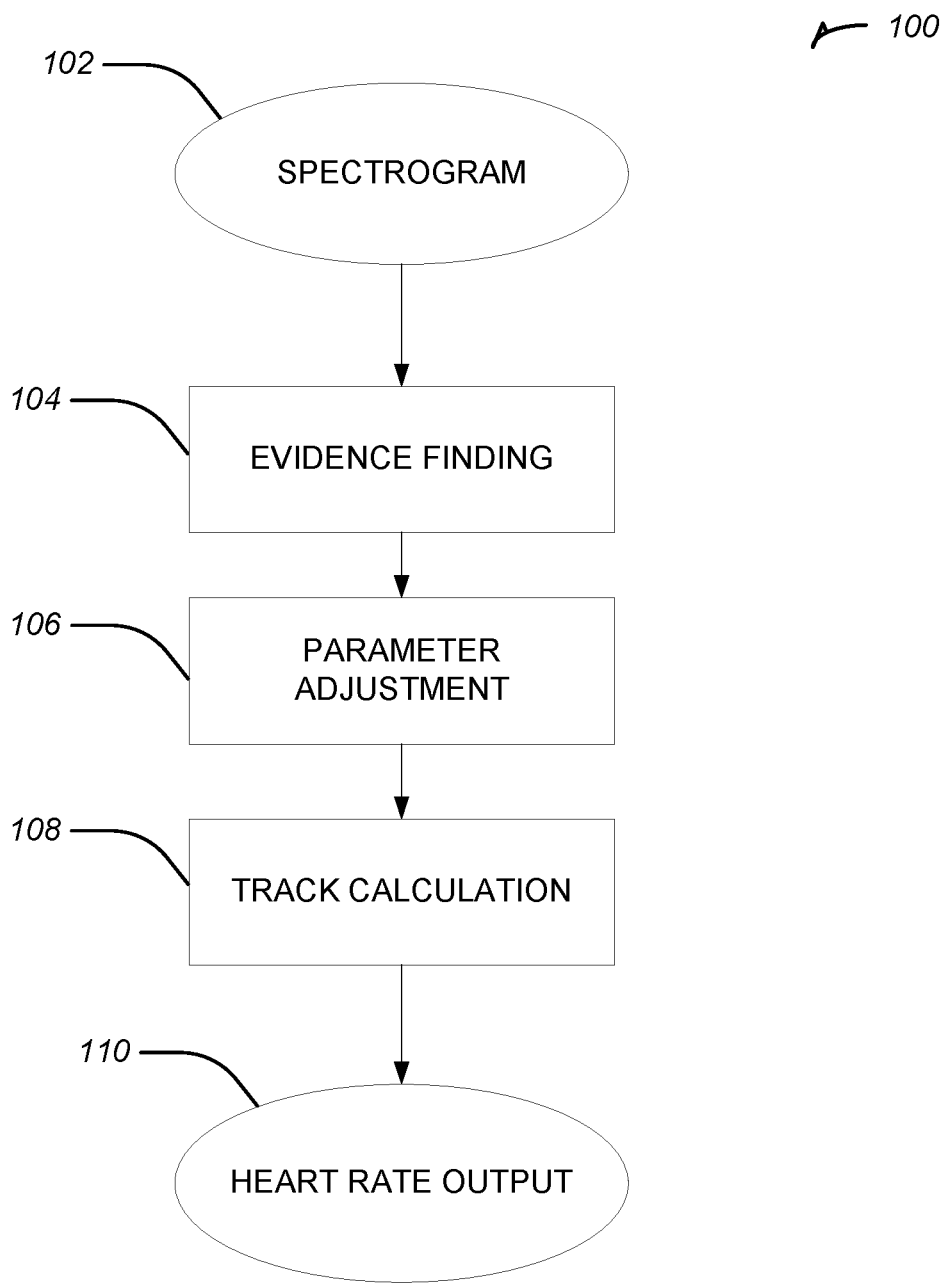
FIG. 1 illustrates a block diagram showing a heart rate monitoring system in accordance with some embodiments.

FIG. 1 illustrates a block diagram showing a heart rate monitoring system 100 in accordance with some embodiments. The system 100 includes a spectrogram block 102, an evidence finding block 104, a parameter adjustment block 106, a track calculation block 108, and a heart rate output block 110.

The spectrogram block 102 includes a spectrum analysis operation to analyze results of PPG signals. The evidence finding block 104 includes a finding evidence operation to determine reasonable frequency components. The parameter adjustment block 106 includes an adjusting transition probability and transition range operation for heart rate index bins. The track calculation block 108 includes a calculating and updating the track probability operation for heart rate index bins, and may include an operation to find the track with a maximum probability. The track calculation block 108 includes a searching operation, near the maximum probability track and a weighting operation to lower the latency. The heart rate output block 110 includes an outputting operation to output the heart rate result.

The heart rate monitoring system 100 may include an improved technique for heart rate monitoring. The improved technique may consider all possible heart rate change paths in a given spectrogram, and may select one with a maximum likelihood. A Hidden Markov Model (HMM) may be used to consider all possible heart rate change paths in a given spectrogram. A parameter adaptation process may make tracking more accurate.

A HMM is a statistical Markov model in which the system being modeled is assumed to be a Markov process with unobserved (i.e., hidden) states. In simpler Markov models (e.g., a Markov chain), the state is directly visible to the observer, and the state transition probabilities are the only parameters. In a HMM, the state is not directly visible, but output, dependent on the state, is visible.

Each frequency bin, $i=1,2,\ldots,N$, of a spectrogram may be modeled as hidden state i, which may represent a random event that a true heart rate equals the frequency corresponding to the bin. So for any second t, there is one hidden state that is true, denoted as $q_t$. As the hidden state is time-varying, the true state may transit between hidden states and forms as a time-varying sequence $q_0, q_1, \ldots, q_{(t-1)}, q_t, q_{(t+1)} \ldots$. The variable $q_t$ is a random variable with its value that may equal the index of true state at time t. The variable q may become a random process with a range of hidden states. A hidden state sequence may be denoted according to properties of a Markov chain, where $P(q_t|q_{t-1} \ldots q_1 q_0) = P(q_t|q_{t-1})$ is the transition probability.

The observation in HMM may include the measured power of each frequency bin in a spectrogram, denoted as o, at the true state the spectra power. In an example, the power, E(i), is likely to be higher, so the conditional probability $P(o_t|q_t=i)$ may be roughly proportional to the power E(i). Using this HMM model with dynamically adjusted and pre-tuned parameters, the probability of any heart rate trajectory may be evaluated. The probability of current hidden states may also be evaluated, and a best estimation of the true heart rate may be determined.

The HMM may be applied and parameters of the HMM may be adjusted adaptively. A frequency component may include a hidden state that transmits to a nearby component with some pre-determined probability, and each state may generate a specified level of power in a corresponding frequency bin of spectra according to some distribution. In an example, a posterior probability of hidden states may be estimated for a given spectrogram. An output may include a real-time heart rate corresponding to a maximum posterior probability. To adapt to quick changes in heart rate and filter out MA interference, rules may be used to modify HMM parameters based on observation and prior knowledge of human heart rate dynamics. By calculating the posterior probability for the frequency components, the improved technique may track the possible paths concurrently and may find the best among them. By adjusting parameter of HMM model adaptively, quickly changing heart rates may be tracked over time more robustly and may reject MA interference.

According to results of a simulation on log data captured using a PPG sensor from 20 human test subjects, the improved technique is 15% more accurate, where mean accuracy may include a percentage of time when the error in heart rate calculations is within ±5%.

Figure 2:
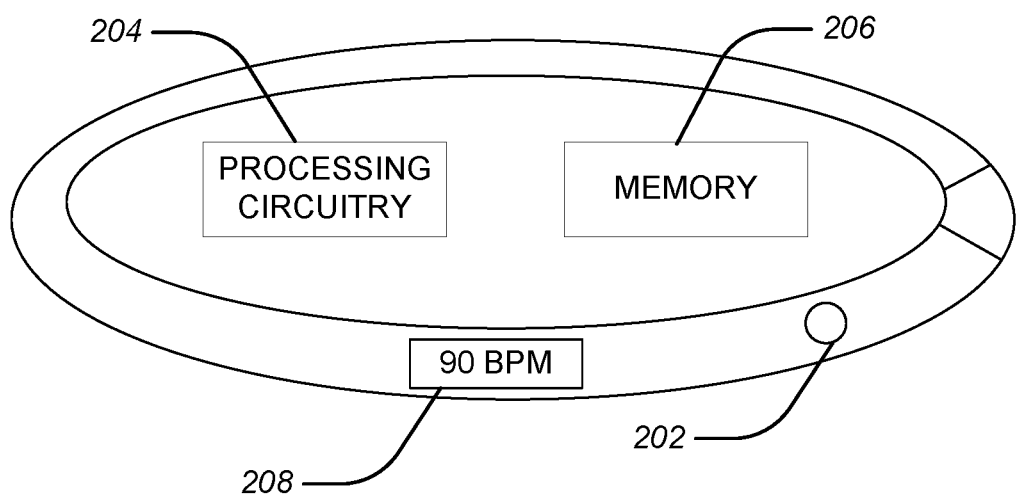
FIG. 2 illustrates a wearable device for heart rate monitoring in accordance with some embodiments.

FIG. 2 illustrates a wearable device 200 for heart rate monitoring in accordance with some embodiments. The techniques described herein may be implemented by an end user device, such as the wearable device 200. The wearable device 200 may include a dedicated heart rate monitor, a smartwatch, or may be integrated into any other wearable device. The wearable device 200 may include a sensor 202, such as an optical heart rate sensor or a pulse oximeter. The sensor 202 may be used to take measurements that may be converted to and output as a spectrogram. The spectrogram may be created from sensor outputs, such as a time-varying one-dimensional continuous electrical signal. The signal may be filtered or amplified by an analog front end (AFE) and converted to a discrete-time digital signal by an analog-to-digital converter (ADC). The converted signal may be sent to a processor to generate a spectrogram from the converted signal. The spectrogram may be output to a processor of the wearable device 200, or may be output to a server or other remote device, such as a mobile phone in wireless connection with the wearable device 200. The spectrogram may be analyzed (at the wearable device 200, the server, or the other remote device) using the techniques described herein to determine a heart rate of a user of the wearable device 200. For example, the spectrogram may be analyzed using the processing circuitry 204. Information may be saved to the memory 206.

The processing circuitry 204 may create a spectrogram from converted signals generated by the sensor 202, the spectrogram including a plurality of bins of represented frequencies corresponding to potential heart rate measurements. The processing circuitry 204 may select a bin of frequencies from the plurality of bins of represented frequencies with an average power that is a maximum average power. The processing circuitry 204 may determine whether a central frequency of the bin of frequencies represents a valid heart rate based on the average power and a past valid heart rate. When the processing circuitry 204 determines that the central frequency represents a valid heart rate, the processing circuitry 204 may output a heart rate corresponding to the frequency, for example on display 208.

Figure 3:
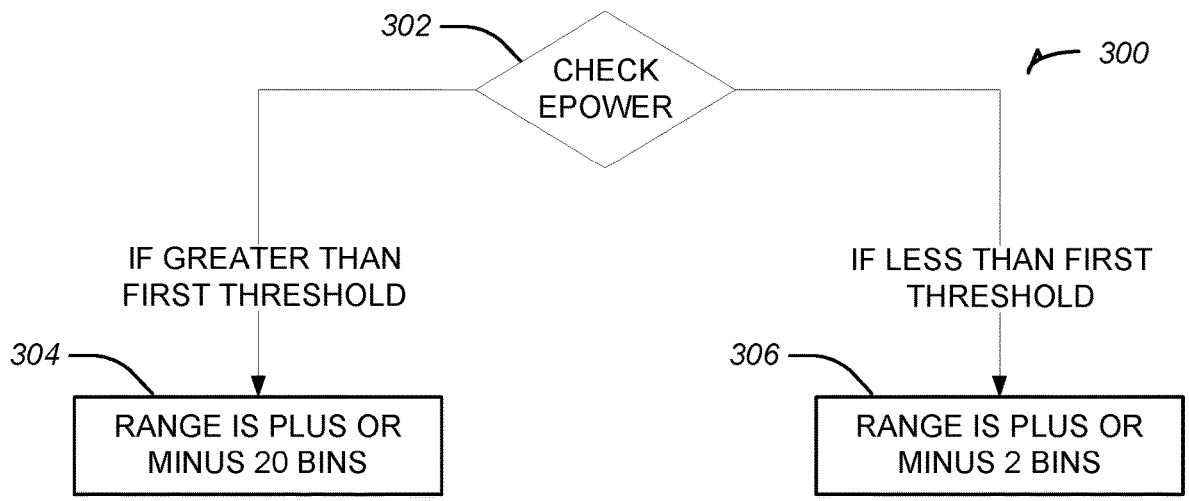
FIG. 3 illustrates a flowchart showing a technique for determining ranges for heart rate measurements in accordance with some embodiments.

FIG. 3 illustrates a flowchart showing a technique 300 for determining ranges for heart rate measurements in accordance with some embodiments.

In an example, possible heart rate ranges may be limited to those usually seen in humans. For example, the heart rate of a person usually below 220 Beats Per Minute (BPM), and above 30 BPM. Typical heart rates are between 50 BPM and 160 BPM, and that range may be used to cover most situations. Using the tighter range of 50-160 BPM may allow for higher accuracy.

Using a spectrogram representing measurements taken at a sensor, spectrogram bins may be determined. Bins may include frequency ranges on the spectrogram. The frequency ranges may include error values around representative frequencies, the representative frequencies corresponding to valid heart rate integer values in BPM. For example, a bin may include frequencies representing BPM between 84.5 and 85.5, with a central frequency representing 85 BPM. In another example, bins may represent other ranges of frequencies, such as frequencies representing BPM between 72.3 and 72.5.

In an example, five neighboring spectrogram bins may be considered, such as those representing BPM 71.5 to 71.7, 71.7 to 71.9, 71.9 to 72.1, 72.1 to 72.3, and 72.3 to 72.5. An average power of each of the five neighboring spectrogram bins may be determined (e.g., representing BPM of 71.6, 71.8, 72, 72.2, and 72.4), of which the central bin may correspond to an integer heart rate (e.g., in the example, 72 BPM). An average power may be determined for a set of five bins for a corresponding heart rate, such as between 50 BPM and 160 BPM. Other frequency bins may be used, such as with narrower frequency ranges (e.g., representing 0.1, 0.01, 0.001, etc. BPM differences) or larger frequency ranges (e.g., representing 0.5, 1, 2, 5, etc. BPM differences).

A frequency bin of the spectrogram with a maximum average power may be determined. The maximum average power may be called an evident power (Epower) for a specified frequency bin, which may be called an evident bin (Ebin). In an example, other frequencies with average power less than the maximum average power may be used. In another example, the maximum average power may correspond to the only frequency used based on the domination of a heart rate signal even when noise is present.

The technique 300 includes checking the Epower for a frequency of a spectrogram at block 302 to determine if the Epower exceeds a first threshold. In an example, the first threshold may include a minimum average power, such as 100.

In an example, the technique 300 may rely on an assumption that a heart rate will not change too quickly in a short period of time. For example, when a heart rate is determined by a technique to be 60 BPM one second and 150 BPM the next second, there is likely an error. The basic change rate of change for a heart rate measured in a technique may be restricted to ±2 frequency bins per second (e.g., corresponding to about ±4 BPM/second). In technique 300, when the Epower is less than the first threshold at block 302, the range may be restricted at block 306.

This parameter may correspond to a number of non-zero probability entries of a HMM transition matrix. The restricted range may help to smooth a heart rate curve, and may reduce influences of isolated noise points on the probability calculation of a possible new heart rate output.

In practice, for example in short-time body-building exercisers, the heart rate may change significantly quicker than usual. Technique 300 includes, when the Epower is determined to exceed the first threshold at block 302, increasing the range to ±20 frequency bins (e.g., corresponding to about ±40 BPM/second). In the HMM transition model, being more precise, the restriction on change rate may be dynamic rather than static. The restriction parameter may be tuned adaptively and automatically in technique 300, including changing from second to second.

If an Ebin is detected with an Epower that exceeds the first threshold, the Epower indicates the existence of a reliable real heart rate at frequency Ebin. The default restriction may be relaxed from ±2 to ±20 frequency bins per second (e.g., corresponding to an increase from about ±4 to ±40 bpm/second). The increased range may correspond to the frequency bin, and for other frequency bins, the restriction may retain the default setting of ±2 frequency bins per second. The technique 300 allows for better tracking of quick heart rate changes when the signal conditions from a sensor are good, and being robust to noise.

For example, consider a current frequency bin of 30. The bin of 30 may be the detected Ebin, which has an Epower greater than the first threshold. The bin of 30 may be changed from a broader range of neighboring states of previous spectra. On the other hand, a frequency bin other than the detected Ebin or one with an Epower lower than the threshold, may be noise. In this frequency bin the change may be restricted to a smaller default range.

For example, Table 1 below shows range restrictions corresponding to technique 300, including an example adaptive transition range adjustment. When Ebin with Epower exceeds some large threshold, such as 100, a first set of bins is used, to allow a large transition in heart rate (such as 20 frequency bins corresponding to about 40 bpm/second); When Ebin with Epower does not exceed the large threshold, a second set of bins is used, to allow for a small transition (such as 2 frequency bins corresponding to about 2 bpm/second).

TABLE 1

| Restriction in transition range | For $E_{BIN}$ with $E_{POWER} > 100$ | Otherwise |
|---|---|---|
| in frequency bins/second unit | ±20 | ±2 |
| in bpm/second unit | ±40 | ±4 |

To determine the likelihood of a state "I" at a time "t," a HMM forward technique may be used. For an observation "o" and a state corresponding to the frequency bin "q," a recursive technique may be used to determine a joint probability of observation history of to of when the current state $q_t$ equals i using Equation 1 below.

$$\alpha_t(i) \stackrel{def}{=} P(o_1 \ldots o_t, q_t = i | \lambda) \quad \text{Equation 1:}$$

Using a HMM technique, Equation 2, below, may be used to determine a probability of a current state using previous neighboring states, such that the transition range and probabilities are determined with respect to a possible previous state.

$$\alpha_t(i) = P(o_t | q_t = i, \lambda) \Sigma_{j=1}^{N} [\alpha_{t-1}(j) \cdot P(q_t = i | q_{t-1} = j, \lambda)] \quad \text{Equation 2:}$$

In Equation 2, an Epower of a bin "j" is an estimate of $P(o_t | q_t = i, \lambda)$, and the transition probability from a previous state j to a current state i is $P(q_t = i | q_{t-1} = j, \lambda)$. In Equation 2, the previous states are used (e.g., the summation is for j=1 to N). In the context of heart rate determination, a transition range restriction may be added to change probabilities outside of a range R to be zero transition probability. The range restriction may include using Equation 3, below.

$$P(q_t = i | q_{t-1} = j, \lambda) = 0 \text{ when } |i - j| > R \quad \text{Equation 3:}$$

Figure 4:
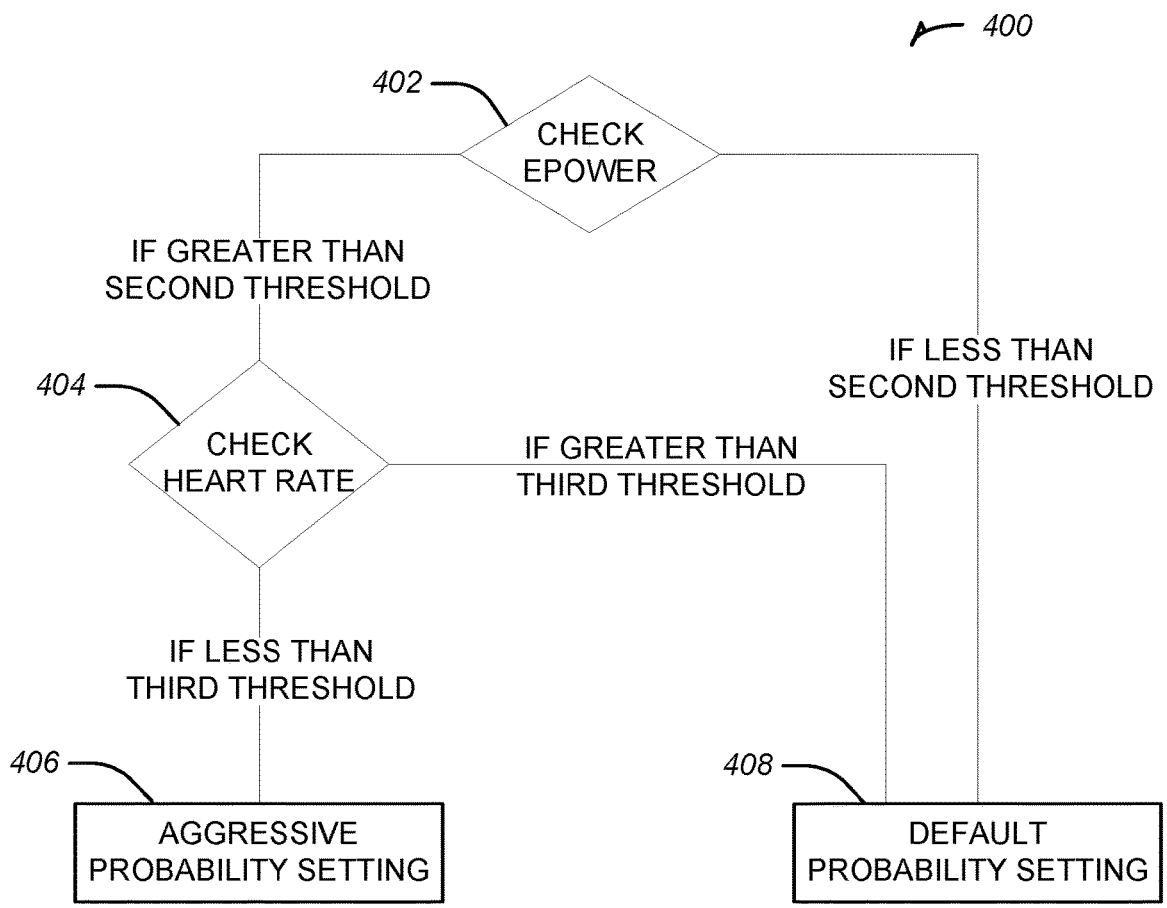
FIG. 4 illustrates a flowchart showing a technique for determining probability for heart rate measurements in accordance with some embodiments.

FIG. 4 illustrates a flowchart showing a technique 400 for determining probability for heart rate measurements in accordance with some embodiments.

When a heart rate is rising, a raw signal from a sensor may often have a quality much worse than a raw signal when the heart rate is falling. One reason behind this phenomenon is that the increasing of a heart rate is often a consequence of body motion, which also introduces motion artifact to signal spectra and may cause noise. It may be more difficult to find an accurate heart rate measurement when the heart rate is rising than when the heart rate is decreasing. A probability may be used to weight frequency bins in a spectrogram to compensate for this difficulty.

The probability for transitions corresponding to the heart rate rising, called $P_{up}$, may be set empirically to be bigger than the probability for transitions corresponding to the heart rate falling, called $P_{down}$, such as to compensate for the possible poor quality of spectrum when the heart rate is increasing.

The probability for transitions corresponding to the heart rate remaining unchanged, called $P_{stay}$, may be set as 1, and may be higher than $P_{up}$ and $P_{down}$. The $P_{stay}$ may be 1 to encourage more a stable heart rate output and remove disturbances.

The $P_{up}$ and $P_{down}$ may be adaptively and automatically tuned in technique 400. The technique 400 includes checking Epower for a specified bin at block 402. Checking Epower at block 402 includes determining whether the Epower is greater than a second threshold (e.g., a threshold different that the first threshold from technique 300), such as 80. The value for the second threshold may be empirically determined from spectrogram measurements. When the Epower is greater than the empirically determined second threshold, the current bin may be considered reliable. In a reliable bin, the $P_{up}$ and $P_{down}$ may become bigger to allow better tracking of quick heart rate changes. The reliable bin setting of probability for transitions may be called an aggressive setting.

In an example, the reliable bin may be further tested to determine if the aggressive setting is proper. Technique 400 includes checking a heart rate at block 404, the heart rate corresponding to the specified bin with the Epower. When the heart rate is determined at block 404 to be smaller than a third threshold (e.g., a heart rate threshold, which may be different than the first or second threshold), such as 130 BPM, the aggressive setting may be used at block 406.

Even if the Epower exceeds the second threshold, there may be small magnitude interference caused by MA, particularly when the heart rate is high (which may be a strong indication of high intensity body motion). In an example, quick heart rate rising may rarely happen when the heart rate is already high. In another example, an increasing heart rate may occur at a decreasing rate. In other words, as a heart rate increases, it may be less likely to increase greater than a previous increase. At block 404, when the heart rate is determined to be above an empirically determined third threshold, a conservative transition policy may be more suitable, and a default setting may be used at block 408. When, at block 402 the Epower is less than the second threshold, the default setting may be used at block 408. Table 2 below illustrates example probability values for an example default setting and an example aggressive setting, for example second and third thresholds.

TABLE 2

|  | Default setting | Aggressive setting $E_{POWER} >= 80$ & heart rate <30 |
|---|---|---|
| $P_{UP}$ | 0.6 | 0.9 |
| $P_{STAY}$ | 1 | 1 |
| $P_{DOWN}$ | 0.4 | 0.7 |

Based on the adjusted parameters, the probability of frequency bins in a spectrogram may be calculated and updated using a HMM forward technique. The frequency bin with a maximum probability may be located, called Hbin. To lower the latency, if Ebin and Hbin are the same bin, a heart rate corresponding to that bin may be output. If Ebin and Hbin are close, (e.g., they represent frequencies corresponding to BPMs that are within a predetermined number of BPMs to each other), the final bin indicating the heart rate to output may be interpolated from Ebin and Hbin. In an example, the interpolated frequency bin may be determined using an Epower of the Ebin and the Hbin as a weight. In another example, Hbin or Ebin may be selected as the final bin. The heart rate corresponding to the final bin may be outputted.

Figure 5:
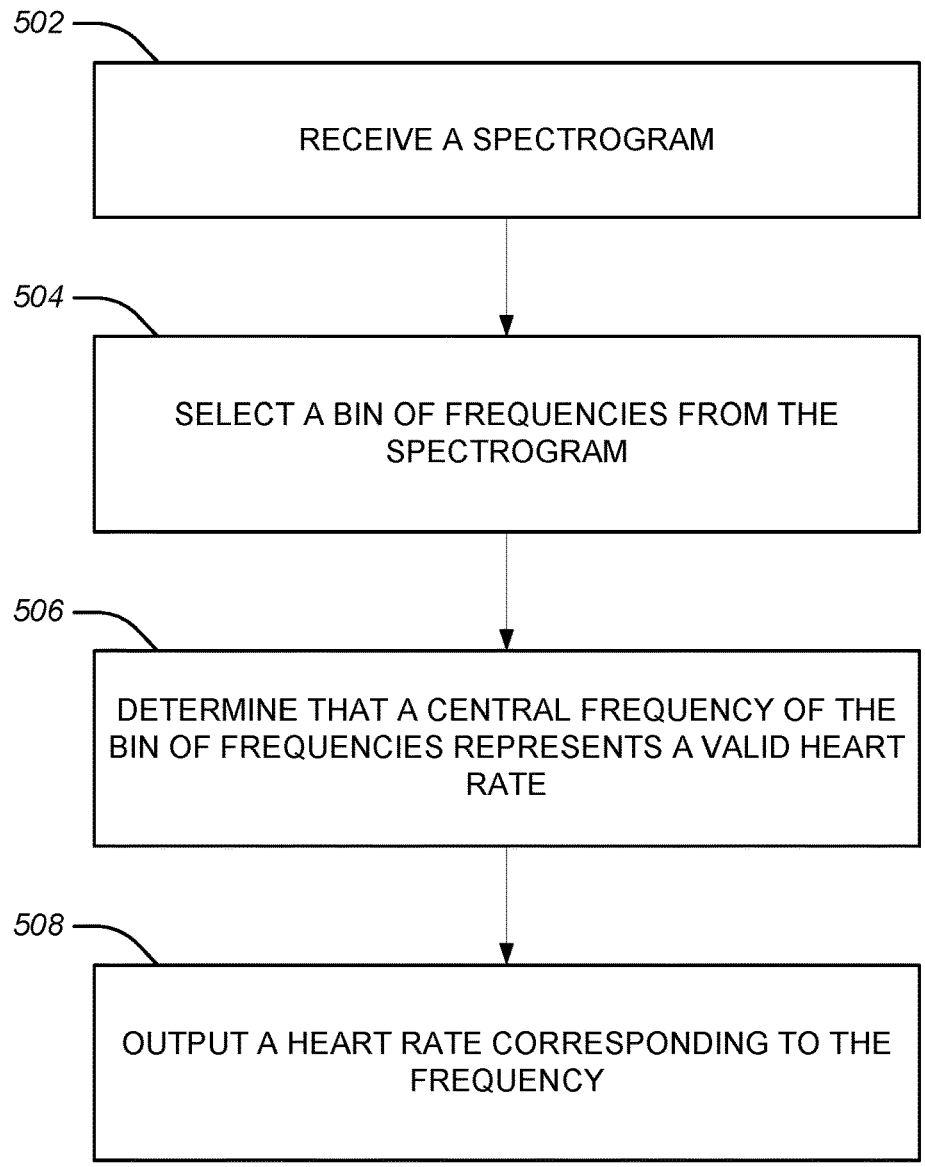
FIG. 5 illustrates a flowchart showing a technique for determining whether a measurement corresponds to a valid heart rate in accordance with some embodiments.

FIG. 5 illustrates a flowchart showing a technique 500 for heart rate monitoring in accordance with some embodiments. The technique 500 includes an operation 502 to receive a spectrogram. The technique 500 includes an operation 504 to select a bin of frequencies from the spectrogram, the bin of frequencies selected from a plurality of bins of represented frequencies represented by the spectrogram. The represented frequencies may correspond to potential heart rate measurements. The bin of frequencies may be selected using HMM.

The technique 500 includes an operation 506 to determine that a central frequency of the bin of frequencies represents a valid heart rate. Operation 506 may include determining that the central frequency includes an average power that is a maximum average power of the spectrogram. When the average power exceeds a first threshold, the central frequency may include a valid heart rate. Operation 506 may include assigning a probability to the central frequency using Table 2, by determining whether the average power exceeds 80, whether the central frequency corresponds to a potential heart rate above 130, and whether the potential heart rate exceeds, equals, or is below a past valid heart rate. Based on the assigned probability, the central frequency may be compared to other central frequencies in the plurality of bins of represented frequencies to determine whether the central frequency represents a valid heart rate, such as when the assigned probability exceeds other probabilities for the other central frequencies. In another example, the assigned probability may be multiplied by the average power for the central frequency, and the resulting value may be compared to an average power multiplied by a probability for the other central frequencies. The technique 500 includes an operation 508 to output a heart rate corresponding to the frequency.

Figure 6:
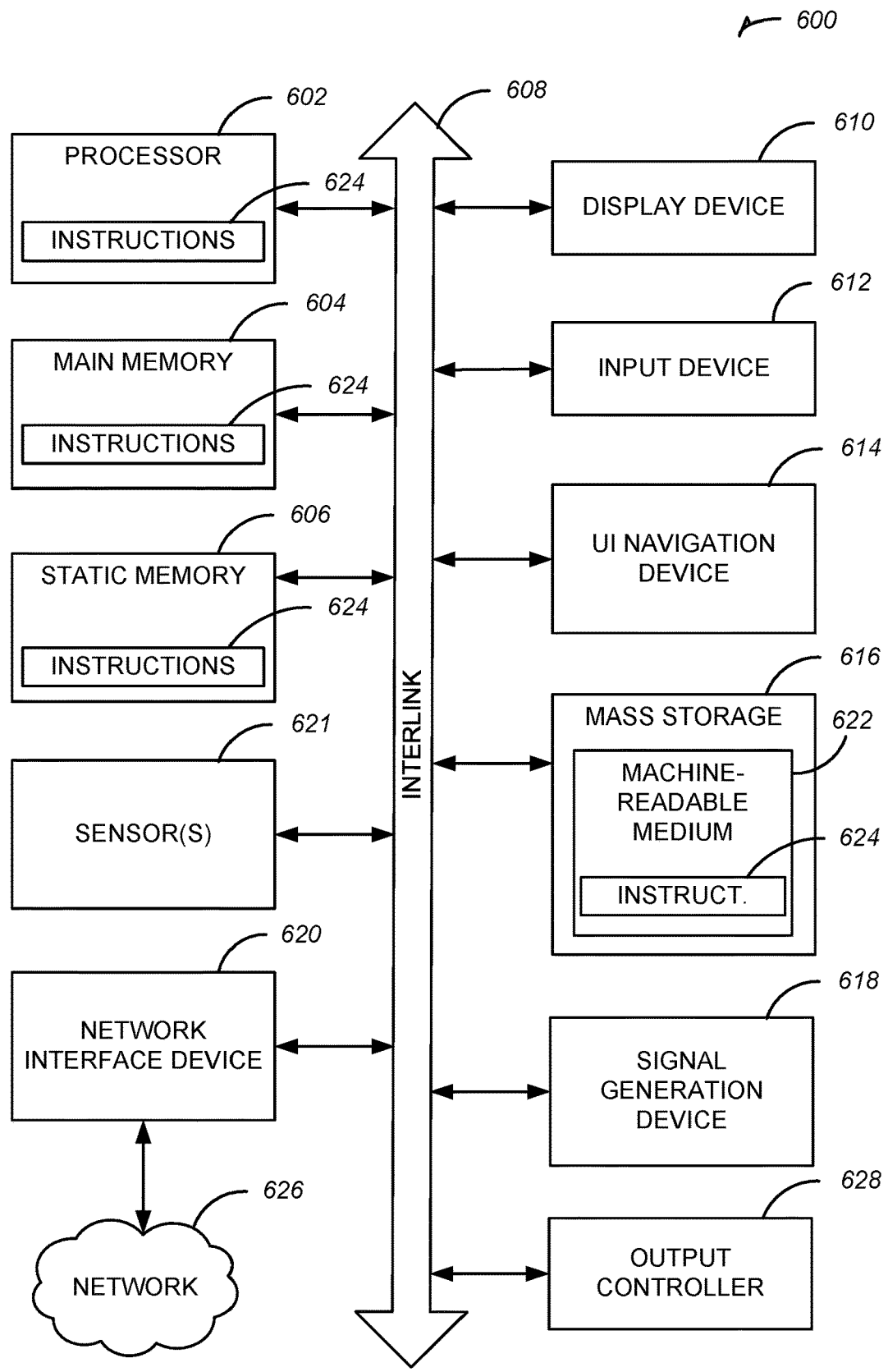
FIG. 6 illustrates generally an example of a block diagram of a machine upon which any one or more of the techniques (e.g., methodologies) discussed herein may perform in accordance with some embodiments.

FIG. 6 illustrates generally an example of a block diagram of a machine 600 upon which any one or more of the techniques (e.g., methodologies) discussed herein may perform in accordance with some embodiments. In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, alphanumeric input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 that is non-transitory on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is a device for heart rate monitoring, the device comprising processing circuitry to: receive a spectrogram including a plurality of bins of represented frequencies corresponding to potential heart rate measurements; select a bin of frequencies from the plurality of bins of represented frequencies with an average power that exceeds average powers of remaining bins of frequencies of the plurality of bins of represented frequencies; determine whether a frequency of the bin of frequencies represents a valid heart rate based on the average power and a past valid heart rate; and in response to determining that the frequency represents a valid heart rate, output a heart rate corresponding to the frequency.

In Example 2, the subject matter of Example 1 optionally includes, further comprising selecting the bin of frequencies using a Hidden Markov Model (HMM).

In Example 3, the subject matter of any one or more of Examples 1-2 optionally include, wherein a first set of bins of frequencies is used to determine the valid heart rate when an evident power for an evident bin exceeds a defined threshold, and wherein a second set of bins of frequencies is used to determine the valid heart rate when the evident power for the evident bin does not exceed the defined threshold, wherein ranges of the second set of bins of frequencies is smaller than ranges of the first set of bins of frequencies.

In Example 4, the subject matter of any one or more of Examples 1-3 optionally include, wherein the frequency represents the valid heart rate when the average power exceeds 100 and the frequency is within 20 of a past frequency representing the past valid heart rate, or wherein the frequency represents the valid heart rate when the average power is below 100 and the frequency is within 2 of a past frequency representing the past valid heart rate.

In Example 5, the subject matter of any one or more of Examples 1-4 optionally include, wherein to determine whether a frequency of the bin of frequencies represents a valid heart rate includes use of a maximum average power, wherein the maximum average power is determined from a probability multiplied by the average power.

In Example 6, the subject matter of Example 5 optionally includes, further comprising determining that the heart rate equals the past valid heart rate and wherein the probability is 100%.

In Example 7, the subject matter of any one or more of Examples 5-6 optionally include, further comprising determining whether the average power exceeds a past average power corresponding to the past valid heart rate, including optionally wherein to determine whether a frequency of the bin of frequencies represents a valid heart rate includes use of a predefined probability, the predefined probability based on whether the average power is less or greater than a predefined threshold, and whether the average power exceeds the past average power.

In Example 8, the subject matter of Example 7 optionally includes, wherein when the average power is less than 80 and the average power exceeds the past average power, the probability is 60%.

In Example 9, the subject matter of any one or more of Examples 7-8 optionally include, wherein when the average power is less than 80 and the average power is below the past average power, the probability is 40%.

In Example 10, the subject matter of any one or more of Examples 7-9 optionally include, further comprising, when the average power is greater than 80, determining whether a heart rate corresponding to the frequency of the bin of frequencies exceeds 130 beats per minute.

In Example 11, the subject matter of Example 10 optionally includes, wherein when the heart rate exceeds 130 beats per minute and is greater than the past valid heart rate, the probability is 90%.

In Example 12, the subject matter of any one or more of Examples 10-11 optionally include, wherein when the heart rate exceeds 130 beats per minute and is less than the past valid heart rate, the probability is 70%.

In Example 13, the subject matter of any one or more of Examples 10-12 optionally include, wherein when the heart rate is below 130 beats per minute and is greater than the past valid heart rate, the probability is 60%.

In Example 14, the subject matter of any one or more of Examples 10-13 optionally include, wherein when the heart rate is below 130 beats per minute and is less than the past valid heart rate, the probability is 40%.

In Example 15, the subject matter of any one or more of Examples 1-14 optionally include, wherein the device is a wearable device.

Example 16 is a method for heart rate monitoring, the method comprising: receiving, at a device, a spectrogram including a plurality of bins of represented frequencies corresponding to potential heart rate measurements; selecting a bin of frequencies from the plurality of bins of represented frequencies with an average power that exceeds average powers of remaining bins of frequencies of the plurality of bins of represented frequencies; determining whether a frequency of the bin of frequencies represents a valid heart rate based on the average power and a past valid heart rate; and in response to determining that the frequency represents a valid heart rate, outputting a heart rate corresponding to the frequency.

In Example 17, the subject matter of Example 16 optionally includes, further comprising selecting the bin of frequencies using a Hidden Markov Model (HMM).

In Example 18, the subject matter of any one or more of Examples 16-17 optionally include, wherein the frequency represents the valid heart rate when the average power exceeds 100 and the frequency is within 20 of a past frequency representing the past valid heart rate.

In Example 19, the subject matter of any one or more of Examples 16-18 optionally include, wherein the frequency represents the valid heart rate when the average power is below 100 and the frequency is within 2 of a past frequency representing the past valid heart rate.

In Example 20, the subject matter of any one or more of Examples 16-19 optionally include, wherein to determine whether a frequency of the bin of frequencies represents a valid heart rate includes use of a maximum average power, wherein the maximum average power is determined from a probability multiplied by the average power.

In Example 21, the subject matter of Example 20 optionally includes, further comprising determining that a heart rate corresponding to the frequency of the bin of frequencies equals the past valid heart rate and wherein the probability is 100%.

In Example 22, the subject matter of any one or more of Examples 20-21 optionally include, further comprising determining whether the average power exceeds a past average power corresponding to the past valid heart rate.

In Example 23, the subject matter of Example 22 optionally includes, wherein when the average power is less than 80 and the average power exceeds the past average power, the probability is 60%.

In Example 24, the subject matter of any one or more of Examples 22-23 optionally include, wherein when the average power is less than 80 and the average power is below the past average power, the probability is 40%.

In Example 25, the subject matter of any one or more of Examples 22-24 optionally include, further comprising, when the average power is greater than 80, determining whether a heart rate corresponding to the frequency of the bin of frequencies exceeds 130 beats per minute.

In Example 26, the subject matter of Example 25 optionally includes, wherein when the heart rate exceeds 130 beats per minute and is greater than the past valid heart rate, the probability is 90%.

In Example 27, the subject matter of any one or more of Examples 25-26 optionally include, wherein when the heart rate exceeds 130 beats per minute and is less than the past valid heart rate, the probability is 70%.

In Example 28, the subject matter of any one or more of Examples 25-27 optionally include, wherein when the heart rate is below 130 beats per minute and is greater than the past valid heart rate, the probability is 60%.

In Example 29, the subject matter of any one or more of Examples 25-28 optionally include, wherein when the heart rate is below 130 beats per minute and is less than the past valid heart rate, the probability is 40%.

In Example 30, the subject matter of any one or more of Examples 16-29 optionally include, wherein the device is a wearable device.

Example 31 is at least one machine-readable medium including instructions for operation of a computing system, which when executed by a machine, cause the machine to perform operations of any of the methods of Examples 16-30.

Example 32 is an apparatus comprising means for performing any of the methods of Examples 16-30.

Example 33 is at least one machine readable medium including instructions that, when executed, cause the machine to perform operations for heart rate monitoring, the operations comprising: receiving, at a device, a spectrogram including a plurality of bins of represented frequencies corresponding to potential heart rate measurements; selecting a bin of frequencies from the plurality of bins of represented frequencies with an average power that exceeds average powers of remaining bins of frequencies of the plurality of bins of represented frequencies; determining whether a frequency of the bin of frequencies represents a valid heart rate based on the average power and a past valid heart rate; and in response to determining that the frequency represents a valid heart rate, outputting a heart rate corresponding to the frequency.

In Example 34, the subject matter of Example 33 optionally includes, further comprising selecting the bin of frequencies using a Hidden Markov Model (HMM).

In Example 35, the subject matter of any one or more of Examples 33-34 optionally include, wherein the frequency represents the valid heart rate when the average power exceeds 100 and the frequency is within 20 of a past frequency representing the past valid heart rate.

In Example 36, the subject matter of any one or more of Examples 33-35 optionally include, wherein the frequency represents the valid heart rate when the average power is below 100 and the frequency is within 2 of a past frequency representing the past valid heart rate.

In Example 37, the subject matter of any one or more of Examples 33-36 optionally include, wherein to determine whether a frequency of the bin of frequencies represents a valid heart rate includes use of a maximum average power, wherein the maximum average power is determined from a probability multiplied by the average power.

In Example 38, the subject matter of Example 37 optionally includes, further comprising determining that a heart rate corresponding to the frequency of the bin of frequencies equals the past valid heart rate and wherein the probability is 100%.

In Example 39, the subject matter of any one or more of Examples 37-38 optionally include, further comprising determining whether the average power exceeds a past average power corresponding to the past valid heart rate.

In Example 40, the subject matter of Example 39 optionally includes, wherein when the average power is less than 80 and the average power exceeds the past average power, the probability is 60%.

In Example 41, the subject matter of any one or more of Examples 39-40 optionally include, wherein when the average power is less than 80 and the average power is below the past average power, the probability is 40%.

In Example 42, the subject matter of any one or more of Examples 39-41 optionally include, further comprising, when the average power is greater than 80, determining whether a heart rate corresponding to the frequency of the bin of frequencies exceeds 130 beats per minute.

In Example 43, the subject matter of Example 42 optionally includes, wherein when the heart rate exceeds 130 beats per minute and is greater than the past valid heart rate, the probability is 90%.

In Example 44, the subject matter of any one or more of Examples 42-43 optionally include, wherein when the heart rate exceeds 130 beats per minute and is less than the past valid heart rate, the probability is 70%.

In Example 45, the subject matter of any one or more of Examples 42-44 optionally include, wherein when the heart rate is below 130 beats per minute and is greater than the past valid heart rate, the probability is 60%.

In Example 46, the subject matter of any one or more of Examples 42-45 optionally include, wherein when the heart rate is below 130 beats per minute and is less than the past valid heart rate, the probability is 40%.

In Example 47, the subject matter of any one or more of Examples 33-46 optionally include, wherein the device is a wearable device.

Example 48 is an apparatus for heart rate monitoring, the apparatus comprising: means for receiving, at a device, a spectrogram including a plurality of bins of represented frequencies corresponding to potential heart rate measurements; means for selecting a bin of frequencies from the plurality of bins of represented frequencies with an average power that exceeds average powers of remaining bins of frequencies of the plurality of bins of represented frequencies; means for determining whether a frequency of the bin of frequencies represents a valid heart rate based on the average power and a past valid heart rate; and in response to determining that the frequency represents a valid heart rate, means for outputting a heart rate corresponding to the frequency.

In Example 49, the subject matter of Example 48 optionally includes, further comprising means for selecting the bin of frequencies using a Hidden Markov Model (HMM).

In Example 50, the subject matter of any one or more of Examples 48-49 optionally include, wherein the frequency represents the valid heart rate when the average power exceeds 100 and the frequency is within 20 of a past frequency representing the past valid heart rate.

In Example 51, the subject matter of any one or more of Examples 48-50 optionally include, wherein the frequency represents the valid heart rate when the average power is below 100 and the frequency is within 2 of a past frequency representing the past valid heart rate.

In Example 52, the subject matter of any one or more of Examples 48-51 optionally include, wherein to determine whether a frequency of the bin of frequencies represents a valid heart rate includes use of a maximum average power, wherein the maximum average power is determined from a probability multiplied by the average power.

In Example 53, the subject matter of Example 52 optionally includes, further comprising means for determining that a heart rate corresponding to the frequency of the bin of frequencies equals the past valid heart rate and wherein the probability is 100%.

In Example 54, the subject matter of any one or more of Examples 52-53 optionally include, further comprising means for determining whether the average power exceeds a past average power corresponding to the past valid heart rate.

In Example 55, the subject matter of Example 54 optionally includes, wherein when the average power is less than 80 and the average power exceeds the past average power, the probability is 60%.

In Example 56, the subject matter of any one or more of Examples 54-55 optionally include, wherein when the average power is less than 80 and the average power is below the past average power, the probability is 40%.

In Example 57, the subject matter of any one or more of Examples 54-56 optionally include, further comprising, when the average power is greater than 80, means for determining whether a heart rate corresponding to the frequency of the bin of frequencies exceeds 130 beats per minute.

In Example 58, the subject matter of Example 57 optionally includes, wherein when the heart rate exceeds 130 beats per minute and is greater than the past valid heart rate, the probability is 90%.

In Example 59, the subject matter of any one or more of Examples 57-58 optionally include, wherein when the heart rate exceeds 130 beats per minute and is less than the past valid heart rate, the probability is 70%.

In Example 60, the subject matter of any one or more of Examples 57-59 optionally include, wherein when the heart rate is below 130 beats per minute and is greater than the past valid heart rate, the probability is 60%.

In Example 61, the subject matter of any one or more of Examples 57-60 optionally include, wherein when the heart rate is below 130 beats per minute and is less than the past valid heart rate, the probability is 40%.

In Example 62, the subject matter of any one or more of Examples 48-61 optionally include, wherein the device is a wearable device.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A device for heart rate monitoring, the device comprising processing circuitry to:
receive a spectrogram including a plurality of bins of represented frequencies corresponding to potential heart rate measurements, wherein the potential heart rate measurements correspond to one or more optical signals;
select a bin of frequencies from the plurality of bins of represented frequencies with an average power that exceeds average powers of one or more remaining bins of frequencies of the plurality of bins of represented frequencies;
determine whether a frequency of the bin of frequencies represents a valid heart rate based on the average power and a past valid heart rate; and
in response to determining that the frequency represents a valid heart rate, output a heart rate corresponding to the frequency,
wherein a first set of bins of frequencies is used to determine the valid heart rate when an evident power for an evident bin exceeds a defined threshold, and wherein a second set of bins of frequencies is used to determine the valid heart rate when the evident power for the evident bin does not exceed the defined threshold, wherein ranges of the second set of bins of frequencies is smaller than ranges of the first set of bins of frequencies.

2. The device of claim 1, further comprising selecting the bin of frequencies using a Hidden Markov Model (HMM).

3. The device of claim 1, wherein the frequency represents the valid heart rate when the average evident power exceeds 100 and the frequency is within 20 beats per minute of a past frequency representing the past valid heart rate.

4. The device of claim 1, wherein the frequency represents the valid heart rate when the average evident power is below 100 and the frequency is within 2 beats per minute of a past frequency representing the past valid heart rate.

5. The device of claim 1, wherein to determine whether a frequency of the bin of frequencies represents a valid heart rate includes use of a maximum average power, wherein the maximum average power is determined from a probability multiplied by the average power.

6. The device of claim 5, wherein the probability is 100% when it is determined that the heart rate equals the past valid heart rate.

7. The device of claim 5, further comprising determining whether the average power exceeds a past average power corresponding to the past valid heart rate.

8. The device of claim 7, wherein to determine whether a frequency of the bin of frequencies represents a valid heart rate includes use of a predefined probability, the predefined probability based on whether the average power is less or greater than a predefined threshold, and whether the average power exceeds the past average power.

9. The device of claim 7, wherein when the average power is less than 80 and the average power exceeds the past average power, the probability is 60%.

10. The device of claim 7, wherein when the average power is less than 80 and the average power is below the past average power, the probability is 40%.

11. The device of claim 7, further comprising, when the average power is greater than 80, determining whether a heart rate corresponding to the frequency of the bin of frequencies exceeds 130 beats per minute.

12. The device of claim 11, wherein when the heart rate exceeds 130 beats per minute and is greater than the past valid heart rate, the probability is 90%.

13. The device of claim 11, wherein when the heart rate exceeds 130 beats per minute and is less than the past valid heart rate, the probability is 70%.

14. The device of claim 1, wherein the device is a wearable device.

15. A method for heart rate monitoring, the method comprising:
receiving, at a device, a spectrogram including a plurality of bins of represented frequencies corresponding to potential heart rate measurements, wherein the potential heart rate measurements correspond to one or more optical signals;
selecting a bin of frequencies from the plurality of bins of represented frequencies with an average power that exceeds average powers of remaining bins of frequencies of the plurality of bins of represented frequencies;
determining whether a frequency of the bin of frequencies represents a valid heart rate based on the average power and a past valid heart rate; and
in response to determining that the frequency represents a valid heart rate, outputting a heart rate corresponding to the frequency,
wherein a first set of bins of frequencies is used to determine the valid heart rate when an evident power for an evident bin exceeds a defined threshold, and wherein a second set of bins of frequencies is used to determine the valid heart rate when the evident power for the evident bin does not exceed the defined threshold, wherein ranges of the second set of bins of frequencies is smaller than ranges of the first set of bins of frequencies.

16. The method of claim 15, further comprising selecting the bin of frequencies using a Hidden Markov Model (HMM).

17. The method of claim 15, wherein the frequency represents the valid heart rate when the average evident power exceeds 100 and the frequency is within 20 beats per minute of a past frequency representing the past valid heart rate.

18. At least one non-transitory machine readable medium including instructions that, when executed, cause the machine to perform operations for heart rate monitoring, the operations comprising:
receiving, at a device, a spectrogram including a plurality of bins of represented frequencies corresponding to potential heart rate measurements, wherein the potential heart rate measurements correspond to optical signals;
selecting a bin of frequencies from the plurality of bins of represented frequencies with an average power that exceeds average powers of remaining bins of frequencies of the plurality of bins of represented frequencies;
determining whether a frequency of the bin of frequencies represents a valid heart rate based on the average power and a past valid heart rate; and
in response to determining that the frequency represents a valid heart rate, outputting a heart rate corresponding to the frequency,
wherein a first set of bins of frequencies is used to determine the valid heart rate when an evident power for an evident bin exceeds a defined threshold, and wherein a second set of bins of frequencies is used to determine the valid heart rate when the evident power for the evident bin does not exceed the defined threshold, wherein ranges of the second set of bins of frequencies is smaller than ranges of the first set of bins of frequencies.

19. The at least one machine readable medium of claim 18, further comprising selecting the bin of frequencies using a Hidden Markov Model (HMM).

20. The at least one machine readable medium of claim 18, wherein the frequency represents the valid heart rate when the average evident power exceeds 100 and the frequency is within 20 beats per minute of a past frequency representing the past valid heart rate.

21. The at least one machine readable medium of claim 18, wherein the frequency represents the valid heart rate when the average evident power is below 100 and the frequency is within 2 beats per minute of a past frequency representing the past valid heart rate.

22. The at least one machine readable medium of claim 18, wherein to determine whether a frequency of the bin of frequencies represents a valid heart rate includes use of a maximum average power, wherein the maximum average power is determined from includes a probability multiplied by the average power.

23. The at least one machine readable medium of claim 22, further comprising determining whether the average power exceeds a past average power corresponding to the past valid heart rate.

24. The at least one machine readable medium of claim 23, further comprising, when the average power is greater than 80, determining whether a heart rate corresponding to the frequency of the bin of frequencies exceeds 130 beats per minute.

* * * * *